United States Patent [19]

Boden et al.

[11] 4,402,985

[45] Sep. 6, 1983

[54] FLAVORING WITH CYCLIC CARBONATE

[75] Inventors: Richard M. Boden, Monmouth Beach; Michael Licciardello, Farmingdale, both of N.J.

[73] Assignee: International Flavors & Fragrances Inc., New York, N.Y.

[21] Appl. No.: 396,249

[22] Filed: Jul. 8, 1982

Related U.S. Application Data

[62] Division of Ser. No. 329,212, Dec. 10, 1981, abandoned.

[51] Int. Cl.$^3$ ............................................. A23L 1/226
[52] U.S. Cl. ...................................... 426/3; 426/536; 426/538; 549/228; 252/522 R; 131/277
[58] Field of Search ........................... 426/536, 538, 3

[56] References Cited

U.S. PATENT DOCUMENTS 3,086,024  4/1963  Braun et al. .......................... 549/228

OTHER PUBLICATIONS

Furia et al., Fenaroli's Handbook of Flavor Ingredients, 2nd Ed., 1975 CRC Press: Cleveland, Ohio, p. 477.

*Primary Examiner*—Joseph M. Golian
*Attorney, Agent, or Firm*—Arthur L. Liberman

[57] ABSTRACT

Described is cyclic carbonate, 4-isopropyl-5,5-dimethyl-m-dioxan-2-one and organoleptic uses thereof in augmenting or enhancing the aroma or taste of consumable materials, foodstuffs, chewing gums, toothpastes, medicinal products, smoking tobaccos, perfume compositions, colognes, perfumed articles (e.g., solid or liquid anionic, cationic, nonionic or zwitterionic detergents, fabric softeners, perfumed polymers and cosmetic powders) smoking tobaccos and smoking tobacco articles.

3 Claims, 3 Drawing Figures

FIG.1
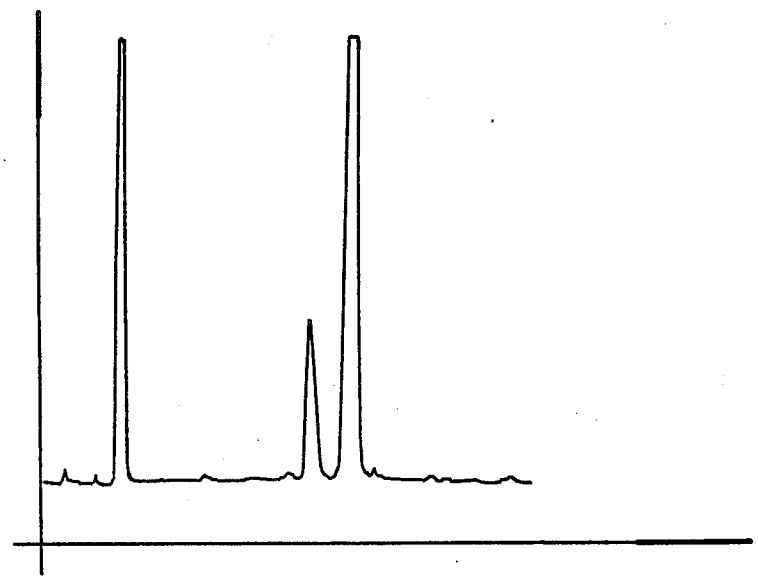
GLC PROFILE FOR EXAMPLE I.
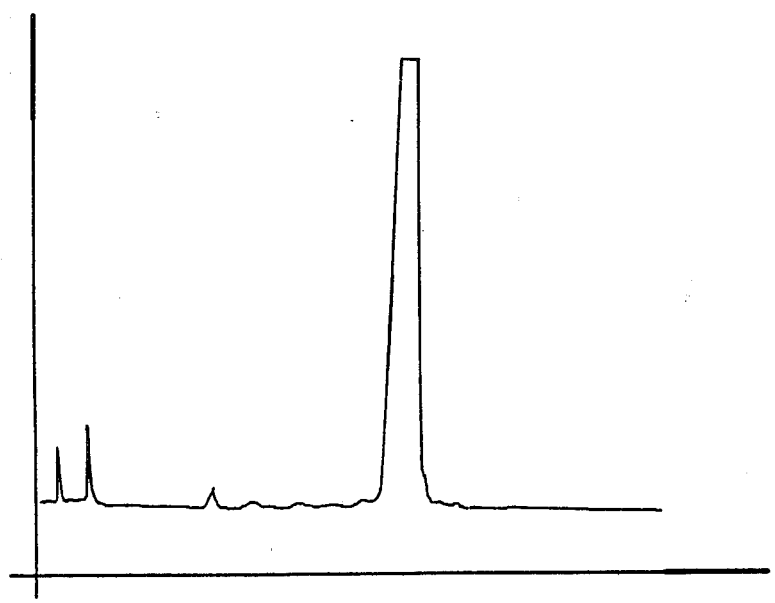
GLC PROFILE FOR EXAMPLE II.
FIG.2

NMR SPECTRUM FOR EXAMPLE II.

FLAVORING WITH CYCLIC CARBONATE

This is a divisional of application Ser. No. 329,212, filed Dec. 10, 1981 now abandoned.

BACKGROUND OF THE INVENTION

The instant invention provides the novel cyclic carbonate defined according to the structure:

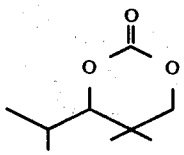

or the stereoisomers defined according to the structures:

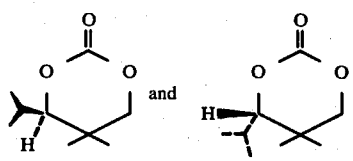

and uses thereof in augmenting or enhancing the aroma or taste of consumable materials.

Materials which can provide coumarin-like and tobacco bark-like aroma nuances are well known in the art of perfumery. Many of the natural substances which provide such fragrances and contribute the desired nuances to perfumery compositions are high in cost, vary in quality from one batch to another and/or are generally subject to the usual variations of natural products.

Materials which can provide woody and cinnamon-like aroma and taste nuances are well known in the art of flavoring for foodstuffs, chewing gums, medicinal products, toothpastes and chewing tobacco. Many of the natural substances which provide such flavor and aroma nuances and contribute the desired nuances to foodstuff compositions, chewing compositions, toothpaste compositions, medicinal product compositions and chewing tobacco compositions are high in cost, vary in quality from one batch to another and/or are generally subject to the usual variations of natural products.

Materials which can provide, prior to smoking in smoking tobacco compositions, sweet, vanilla, coumarin-like, fruity and cinnamon bark-like aroma and taste nuances and on smoking, sweet, fruity and Virginia tobacco-like aroma and taste nuances (with simultaneous enhancing of flue-cured notes) are well known and highly desirable in the art of flavoring smoking tobacco and smoking tobacco articles. Many of the natural substances which provide such aroma and taste nuances to smoking tobacco compositions and smoking tobacco articles are high in cost, vary in quality from one batch to another and/or are generally subject to the usual variations of natural products.

The prior art contains a large number of teachings regarding the use of organic carbonates in augmenting or enhancing the aroma of perfumes. Thus, U.S. Pat. No. 4,033,993 discloses the use of organic carbonates defined according to the structure:

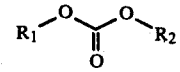

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynyl having from 2 to 5 carbon atoms. U.S. Pat. No. 4,033,993 describes, for example, methyl-1-ethynycyclohexyl carbonate having a fruity, herbal complex odor and distinct fragrance of dill. In addition, U.S. Pat. No. 4,033,993 describes methyl cyclooctyl carbonate as having an herbal, natural and complex fragrance which is distinguished by a strong and long clinging flowery jasmine scent and further indicates its use in jasmine perfume compositions. U.S. Pat. No. 4,033,993 describes the preparation of the compounds defined according to the structure:

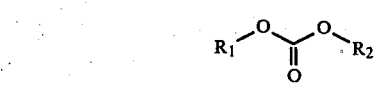

according to the reaction:

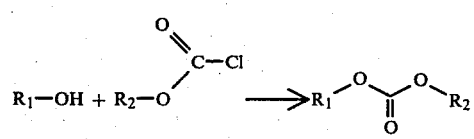

where $R_1$ and $R_2$ are defined as above.

In addition, U.S. Pat. No. 4,080,309 describes the perfume use of the carbonates defined according to the structure:

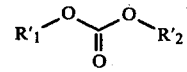

wherein $R_1'$ is a moiety having from 8 to 12 carbon atoms selected from the group consisting of alkylcyclohexyl, alkenylcyclohexyl, alkynylcyclohexyl and cycloalkyl and $R_2'$ is a moiety selected from the group consisting of alkyl having from 1 to 5 carbon atoms, alkenyl having from 2 to 5 carbon atoms and alkynyl having from 2 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of 4,080,309 are indicated to be prepared according to the reaction:

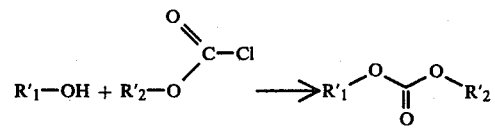

Another aspect of our invention lies in the novel diester used for preparing the cyclic carbonate of our invention. This diester has the structure:

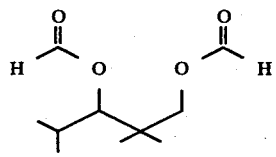

and is a "diformate".

The diisobutyrate having the structure:

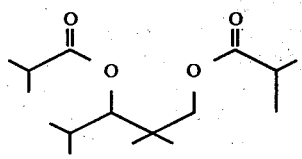

is known in the prior art particularly for use in the plastics industry as a plasticizer for vinyl chloride resins as more particularly described in Japanese Patent No. J8 1039297 abstracted in the Japanese Patents Report, Section Ch:Chemical, Volume 81, No. 38 issued Oct. 16, 1981 at page 37 (published by DERWENT PUBLICATIONS LTD., Rochdale House, 128 Theobalds Road, London WCIX 8RP England) and abstracted thusly:

(A60-E17-(A14)  J8 1039297

2,2,4-Trimethyl-1,3-pentane:diol di:isobutyrate prodn.—by ester-exchanging 2,2,4-tri:methyl:1,3-pentane diol or 3-hydroxy-2,2,4-tri:methyl-pentyl isobutyrate, with isobutyl isobutyrate.

2,2,4-Trimethyl-1,3-pentanediol diisobutylate (I) is produced by ester-exchanging 2,2,4-trimethyl-1,3-pentanediol and/or 3-hydroxy-2,2,4-trimethylpentyl iobutylate, and isobutyl isobutylate at 120–250 deg. C. in the presence of organic Sn cpds. or organic Ti cpds. as catalyst.

(I) is obtd. rapidly in high yields, for use as the plasticisier for vinyl chloride resins, partic, vinyl chloride paste resin, 22.9.77 as 114046 C07c-69/28, 67/03; BO!j-31/12 (11.9.81) CHISSO CORP. (5pp136HM) (J54046708).

Nothing in the prior art however shows the "diformate" having the structure:

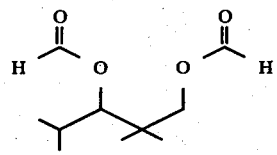

and nothing in the prior art shows such esters useful in the preparation of the cyclic carbonates defined according to the structure:

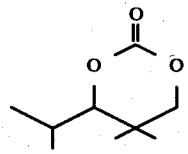

Furthermore, nothing in the prior art shows cyclic carbonates having the structure:

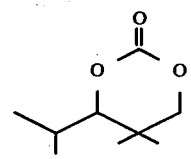

or homologous or analogous compounds useful for their organoleptic properties in augmenting or enhancing the aroma or taste of consumable materials.

BRIEF DESCRIPTION OF THE DRAWINGS

FIG. 1 is the GLC profile for the reaction product of Example I containing the compound having the structure:

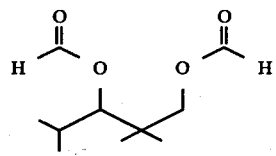

Figure 3:
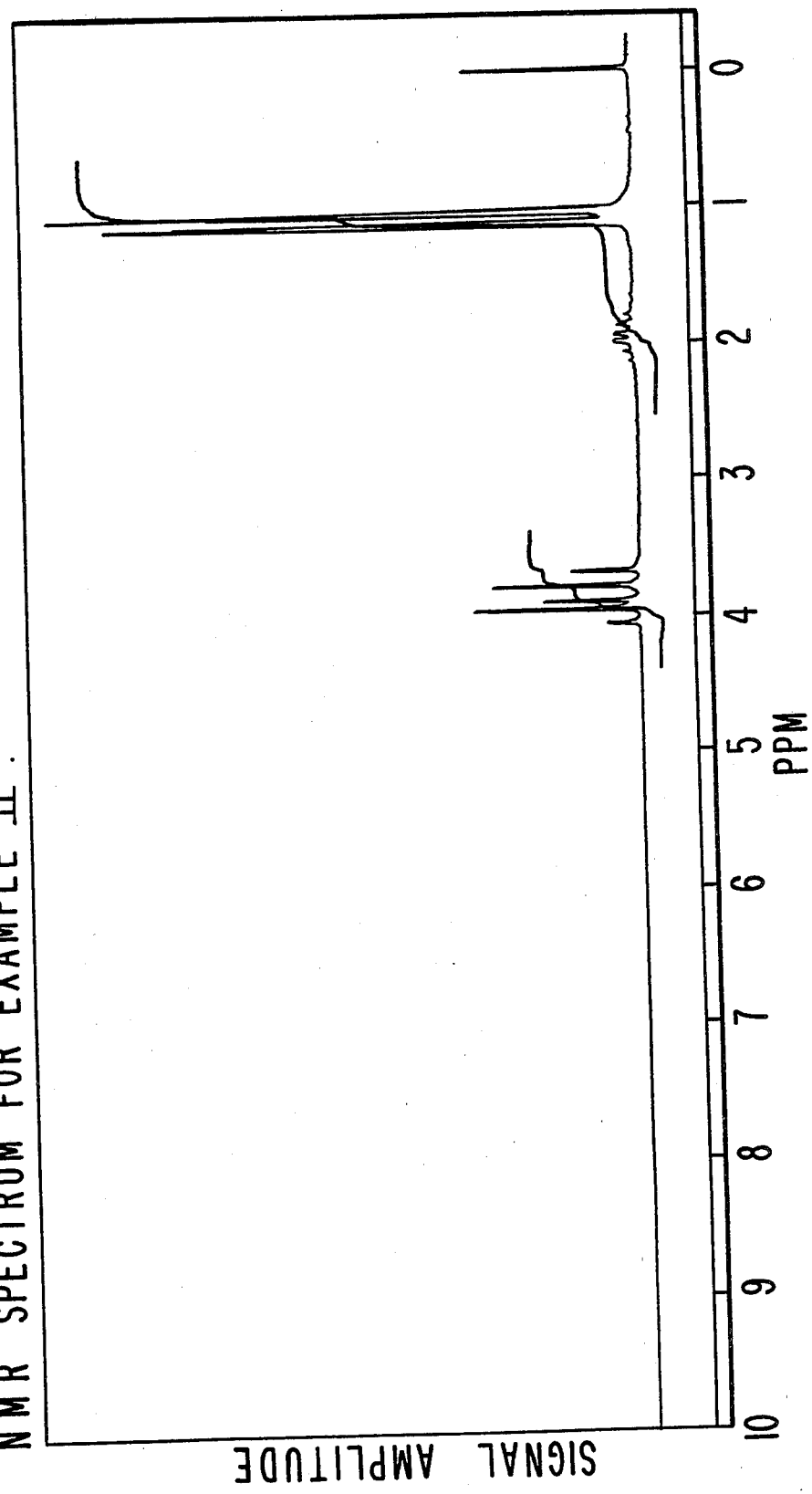

FIG. 2 is the GLC profile for the reaction product of Example II containing the cyclic carbonate having the structure:

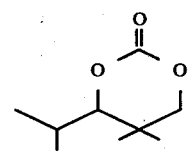

FIG. 3 is the NMR spectrum for the reaction product of Example II containing the compound having the structure:

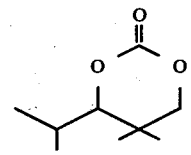

THE INVENTION

It has now been discovered that novel solid and liquid foodstuff, chewing gum, medicinal product, toothpaste and chewing tobacco compositions and flavoring compositions therefor having woody and cinnamon-like aroma and taste nuances; and novel perfume compositions and perfumed articles and colognes having coumarin-like and tobacco bark-like aroma nuances; as well as novel smoking tobacco, flavoring compositions and smoking tobacco articles having, prior to smoking, sweet, vanilla, coumarinic, fruity and cinnamon bark-like aroma and taste nuances; and on smoking sweet, fruity and Virginia tobacco-like aroma and taste nuances (with the flue-cured note being anhanced) can be provided by the use in such consumable materials of the cyclic carbonate defined according to the structure:

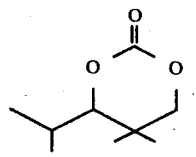

or stereoisomers thereof defined according to one of the structures:

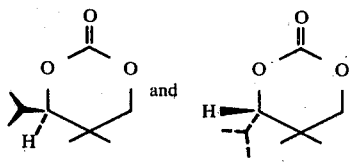

the 4-isopropyl-5,5-dimethyl-m-dioxan-2-one of our invention having the structure:

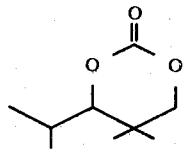

(hereinafter referred to as "the cyclic carbonate") may be prepared by reacting dimethyl carbonate with the "diformate" ester of our invention having the structure:

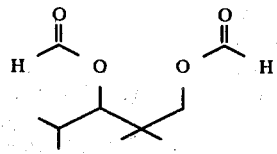

in the presence of an alkali metal alkoxide according to the reaction:

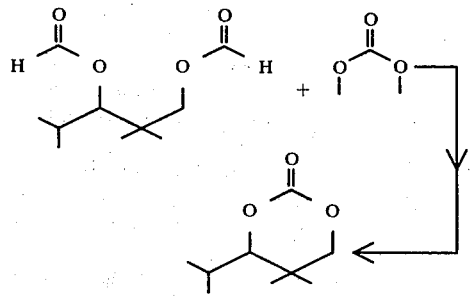

The "diformate" diester compound of our invention having the structure:

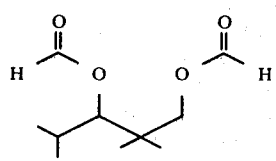

, in turn, is prepared by a esterification of the compound having the structure:

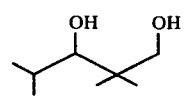

with formic acid in the presence of a protonic acid esterification catalyst such as sulfuric acid according to the reaction:

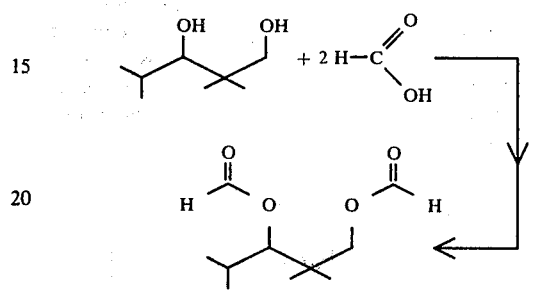

More specifically, the diester of our invention having the structure:

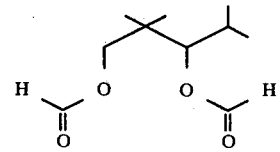

being prepared by reacting formic acid with the diol having the structure:

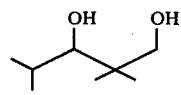

according to the reaction:

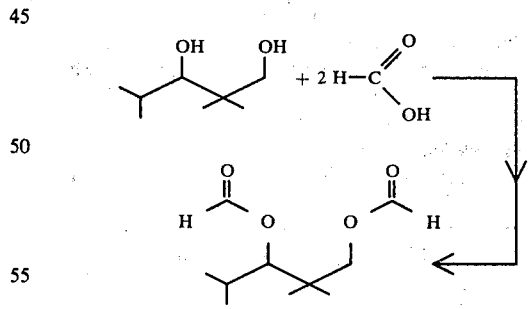

is carried out using a protonic acid catalyst such as concentrated sulfuric acid, concentrated phosphoric acid, concentrated paratoluene sulfonic acid and concentrated methane sulfonic acid in the presence of an inert solvent such as toluene or xylene which will give rise to carrying out the reaction at such temperatures, at reflux.

The temperature of the esterification reaction is preferably in the range of from about 85° C. up to about 115° C., depending upon the solvent used and the concentration of reactants in the solvent. Thus, for example, when toluene is used and when the concentration of total reactants in the solvent is 15–20 moles per liter the reaction temperature is between 90° and 100° C. The mole ratio of formic acid to diol having the structure:

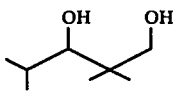

is preferably from 2.5:1 up to about 5:1 with a preferred mole ratio of between 4:1 and 4.5:1. The preferred solvent for use in this reaction is toluene and the preferred protonic acid catalyst is concentrated sulfuric acid. At the end of the reaction the reaction mass is washed with a salt solution and the solvent is stripped off. The reaction mass is then utilized in the subsequent reaction of the diester with the dimethyl carbonate:

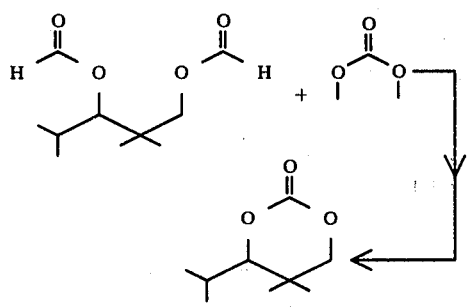

The reaction between the diester having the structure:

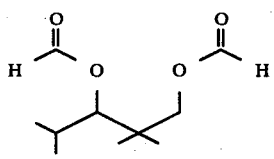

and dimethyl carbonate is carried out in the presence of an alkali metal alkoxide such as sodium methoxide, sodium ethoxide, sodium-t-butoxide, potassium methoxide, potassium ethoxide and potassium-t-butoxide. The reaction between the formate diester and the dimethyl carbonate takes place in the absence of any additional solvent. The mole ratio range of dimethyl carbonate:-formate diester may vary from 3 moles dimethyl carbonate:0.5 moles formate diester down to 1 mole dimethyl carbonate:1 mole formate diester. It is preferred that the mole ratio of dimethyl carbonate:formate diester be about 2:1. The molar concentration in the reaction mass of the alkali metal alkoxide catalyst may vary from about 0.005 up to about 0.01 with a mole ratio of about 0.05 being preferred.

The reaction temperature range may vary from about 50° C. up to about 100° C. and the reaction pressure may vary from atmospheric pressure up to about 10 atmospheres. Higher temperatures of reaction necessitate higher pressures over the reaction mass in order to prevent the reaction product from evaporating therefrom in an uncontrollable fashion.

At the end of the reaction, the reaction product is purified according to standard procedures such as fractional distillation and, if necessary, chromatographic separation as by high pressure liquid chromatography or GLC (vapor phase chromatography).

If desired, the stereoisomers produced having the structures:

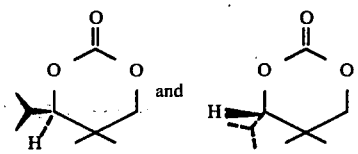

may be separated from one-another by standard separation techniques for separating such stereoismers.

When the cyclic carbonate of our invention is used as a food flavor adjuvant, the nature of the co-ingredients included with the said cyclic carbonate in formulating the product composition will also serve to alter the organoleptic characteristics of the ultimate foodstuff treated therewith. As used herein in regard to flavors, the term "alter" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste." As used herein, the term "foodstuff" includes both solid and liquid ingestible materials which usually do, but need not, have nutritional value. Thus "foodstuffs" include soups, convenience foods, beverages, dairy products, candies, vegetables, cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious, nothing particularly critical resides in the selection thereof. Accordingly, such materials which may, in general, be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agaragar; carrageenan; cellulose and cellulose derivatives, such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers; anti-caking agents, e.g., aluminum calcium sulfate and tribasic calcium phospate; enzymes; yeast foods, e.g., clacium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alphamethyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethylacrolein, n-hexanal, 2-hexenal, cis-3-hexenal, 2-heptanone, 4-(p-hydroxyphenyl)-2-butanone, alphaionone, beta-ionone, methyl-3-butanone, 2-pentanone, 2-pentenal and propanal; alcohols, such as 1-butanal, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha terpineol, cis-terpineol hydrate; esters, such as butyl acetate, ethyl acetate, ethyl acetoacetate, ethyl benzoate, ethyl butyrate, ethyl capronate, ethyl cinnamate, ethyl crotonate, ethyl formate, ethyl isobutyrate, ethyl isovalerate, ethyl-alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl capronate, methyl isobutyrate, alphamethylbutyrate, propyl acetate, amyl acetate, amyl butyrate, benzyl salicylate, dimethyl anthranilate, ethyl methylphenylglycidate, isobutyl cinnamate and terpenyl acetate; essential oils, such as jasmine absolute, rose absolute, orris absolute, lemon essential oil, bulgarian rose, yara yara, natural raspberry oil and vanilla; lactones, sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the cyclic carbonate can be dispersed or admixed to provide a homogeneous medium. In addition, selection of one or more flavoring adjuvants, as well as the the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of high cyclic carbonate employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing a composition merely deficient in natural flavor or aroma. Thus, the primary requirement is that the amount selected should be "effective," i.e., sufficient to alter the organoleptic characteristics of the parent composition, whether foodstuff per se or flavoring composition. Thus, the use of insufficient quantities of high cyclic carbonate will, of course, substantially, vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of high cyclic carbonate ranging from a small but effective amount, e.g., 0.10 parts per million up to about 50 parts per million by weight based on total composition are suitable. Concentrations in excess of the maximum quantity stated are not normally recommended since they fail to provide commensurate enhancement of organoleptic properties. In those instances wherein the cyclic carbonate is added to the foodstuff as an integral component of a flavoring composition, it is of course essential that the total quantity of flavoring composition employed be sufficient to yield an effective cyclic carbonate concentration in the foodstuff product.

Food flavoring compositions prepared in accordance with the present invention preferably contain the high cyclic carbonate in concentrations ranging from about 0.05% up to about 10% by weight based on the total weight of said flavoring composition.

The compositions described herein can be prepared according to conventional techniques well known, as typified by cake batters and vegetable juices, can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the high cyclic carbonate with, for example, gum arabic, gum tragacanth, carrageenan and the like, and thereafter spray-drying the resultant mixture whereby to obtain the particular solid product. Pre-prepared flavor mixes in powder form, e.g., a strawberry-flavored powder mix or a raspberry-flavored powder mix are obtained by mixing the dried solid components, e.g., starch, sugar and the like and the cyclic carbonate in a dry blender until the requisite degree of uniformity is achieved.

It is presently preferred to combine with the cyclic carbonate the following adjuvants:

Vanillin
Maltol

Benzaldehyde
Isovaleraldehyde
3-phenyl-3-pentenal-dimethyl-acetyl
3-phenyl-4-pentenal-dimethyl-acetyl
Cinnamic aldehyde
Phenyl-ethyl alcohol
Oil of cloves
Orange oil
Ethyl vanillin
Oil of bitter almond
Oil of cinnamon bark
Oil of cloves
Oil of cardamom
Oil of nutmeg
Oil of lemon The cyclic carbonate can also be used to improve and augment the organoleptic properties of smoking tobacco and smoking tobacco products. Thus, the said cyclic carbonate will impart, augment or enhance prior to smoking sweet, vanilla, coumarinic, fruity and cinnamon-bark-like aroma and taste nuances; and on smoking sweet, fruity and virginia tobacco-like aroma and taste nuances (with the flue-cured note being enhanced).

The use of level of the cyclic carbonate of our invention in smoking tobacco or in smoking tobacco articles (e.g., in the wrapper, filter or in the smoking tobacco itself) is at the levels of from about 50 parts per million up to about 800 parts per million based on the dry weight of the smoking tobacco or smoking tobacco article. "Tobacco" is used herein includes natural tobaccos such as burley, Turkish tobacco, Maryland tobacco, tobacco-like products such as reconstituted tobacco or homogenized tobacco and tobacco substitutes intended to replace tobacco such as various vegetable leaves for example, lettuce leaves, cabbage leaves and the like.

The cyclic carbonate of our invention in an auxiliary perfume ingredient including for example, one or more alcohols, aldehydes, nitriles, esters, cyclic esters (e.g., lactones and cyclic carbonates other than the cyclic carbonate of our invention) and natural essential oils maybe admixed so that the combined odors of the individual properties produce a pleasant and desired fragrance particularly and preferably in coumarin-like and tobacco bark-like fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, the individual component will contribute its particular olfactory characteristics, but the overall effect of the perfume composition will be the sum of each of the effects of each of the ingredients. Thus, the cyclic carbonate of our invention can be used to alter the aroma characteristics of the perfume composition, for example, by highlighting or moderating the olfactory reaction contributed by another ingredient in the composition.

The amount of cyclic carbonate of our invention which will be effective in perfume compositions depends upon many factors including the other ingredients, their amounts and the effects which are desired. It has been found that perfume compositions containing as little as 0.1% of the cyclic carbonate of our invention or even less and perfume compositions containing as much as 70% of the cyclic carbonate or our invention can be used to impart interesting coumarin-like and tobacco-like aroma nuances to perfumed articles, perfume compositions and colognes. Such perfumed articles include fabric softener compositions, drier-added fabric softener articles, cosmetic powders, talc, solid or liquid anionic, cationic, nonionic or zwitterionic detergents and perfumed polymers. The amount employed can range up to 70% and will depend on considerations of cost, nature of the end product and the effect desired on the finished product and particular fragrance sought.

Thus, the cyclic carbonate of our invention can be used alone or in a perfume composition as an olfactory component, in solid or liquid anionic, cationic, nonionic or zwitterionic detergents (including soaps), perfumed polymers (those which are microporous and those which are macroporous and contain particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer containing an absorbent filler or such as a solid or liquid cationic, anionic, nonionic or zwitterionic detergent or such as a cosmetic powder, as little as 0.01% of the cyclic carbonate of our invention will suffice to impart a coumarin-like, tobacco bark-like aroma. Generally, no more than 2.0% of the cyclic carbonate of our invention is required.

In addition, the perfume compositions of our invention can contain a vehicle or carrier for the cyclic carbonate of our invention alone or with other ingredients. The vehicle can be a liquid such as an alcohol such as ethanol, a glycol such as propylene glycol or the like. The carrier can be an absorbent solid such as a gum (e.g., xanthan gum or gum arabic) or components for encapsulating the composition as by coacervation (using a gelatin) or polymerization around a liquid center (using a urea formaldehyde prepolymer).

The following Example I sets forth a process for preparing the cyclic ester precursor of the cyclic carbonate of our invention. The following Example II sets forth a process for preparing the cyclic carbonate of our invention. The following Example III, et. seq., represent methods for using the cyclic carbonate of our invention for its organoleptic properties.

Unless otherwise indicated, all parts and percentages are by weight.

EXAMPLE I

Preparation of Formic Acid Diester

Reaction:

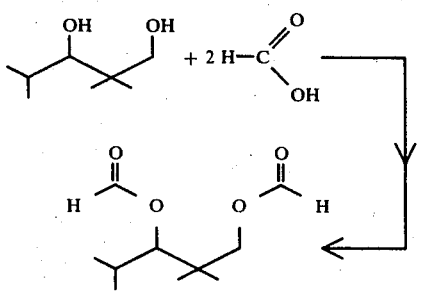

Into a 500 ml reaction flask equipped with heating mantle, stirrer, reflux condenser, Bidwell liquid collection trap and thermometer is placed 90 grams (0.6 moles) of the compound having the structure:

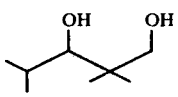

100 ml (2.5 moles) of formic acid; 200 ml toluene and 2 ml 98% sulfuric acid. With stirring the reaction mass is heated to reflux and refluxed over a period of 2 hours while azeotroping water from the reaction mass using the Bidwell trap. The reaction temperature is between 90° and 96° C.

At the end of the reaction the reaction mass is washed with three 250 ml portions of saturated sodium chloride.

The reaction mass is then stripped of toluene and utilized as such in Example II.

FIG. 1 is the GLC profile for the reaction product.

EXAMPLE II

Preparation of
4-Isopropyl-5,5-Dimethyl-M-Dioxan-2-One

Reaction:

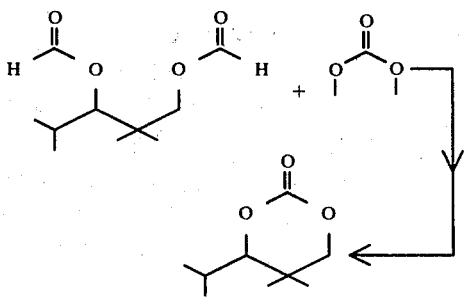

Into a 500 ml reaction flask equipped with heating mantle stirrer, Bidwell trap, reflux condenser, thermometer and nitrogen blanket apparatus, is placed 0.6 moles of the diester prepared according to Example I; 90 grams (1.0 moles) of dimethyl carbonate and 5 grams (0.1 moles) of sodium methoxide. The reaction mass is heated to 80° C. and the methyl formate being formed is distilled out of the reaction mass through the Bidwell trapping apparatus. The reaction mass is stirred at 75°–80° C. over a period of 2 hours at which point and time the reaction is complete.

The reaction mass is washed with three 500 ml portions of water and stripped of solvent and distilled on a microvigrux column yielding the following three fractions.

| Fraction Number | Vapor Temp. | Liquid Temp. | Head Vaccum mm.Hg. | Weight Fraction |
|---|---|---|---|---|
| 1 | 117/138 | 118/133 | 5/5 | 13 |
| 2 | 131 | 137 | 5 | 34 |
| 3 | 137 | 180 | 5 | 13 |

FIG. 2 is the GLC profile for the reaction product prior to distillation.

FIG. 3 is the NMR spectrum for bulked fractions 2 and 3 subsequent to the distillation.

EXAMPLE III

Perfume Composition

The following mixture is prepared:

| Ingredients | Parts by Weight |
|---|---|
| Cyclic carbonate prepared according to Example II (bulked Fractions 2 and 3) | 180 |
| 3-Phenyl-4-pentenal dimethyl acetal | 8 |
| 3-Phenyl-3-pentenal dimethyl acetal | 10 |
| Ylang extra | 10 |
| Geraniol coeur | 50 |
| Citronellol coeur | 100 |
| Dimethyl benzyl carbinol | 15 |
| Phenyl ethyl alcohol coeur | 50 |
| Hexyl cinnamic aldehyde | 40 |
| 2-n-heptyl-cyclopentanone | 5 |
| Diels alder addition product of cyclopentadiene and 3-methyl-3-penten-2-one having the structure: | 30 |
| Myrcenyl acetate | 1 |
| Geranonitrile | 20 |
| Geranyl acetate | 30 |
| Lavender | 20 |
| Nerole | 10 |
| Tetrahydro muguol | 60 |
| 4-(4-methyl, 4-hydroxy amyl)Δ3-cyclohexene carboxaldehyde | 50 |

The cyclic carbonate of Example II imparts to this green Nasturtian fragrance a tobacco-like coumarin-like aroma nuance creating a novel esthetically pleasing blend which can be described as tobacco bark-like, cinnamon-like, green, balsamic, with rosey undertones.

EXAMPLE IV

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| Cyclic carbonate prepared according to Example II (bulked Fractions 2 and 3) | Coumarin-like, tobacco bark-like aroma. |
| Perfume compositions of | Tobacco bark-like, cinnamon- |

TABLE I-continued

| Substance | Aroma Description |
|---|---|
| Example III | like, green, balsamic, with rosey undertones. |

EXAMPLE V

Perfumed Liquid Detergents

Concentrated liquid detergents (Lysine salt of n-dodecylbenzene sulfonic acid as more specifically described in U.S. Pat. No. 3,948,818, issued on April 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

Preparation of Colognes and Handkerchief Perfumes

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

Preparation of Soap Compositions

One hundred grams of soap chips [per sample] (IVORY ®, produced by the Procter & Gamble Company of Cincinnati, Ohio), are each mixed with one gram samples of substances as set forth in Table I of Example IV until homogenous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table I of Example IV.

EXAMPLE VIII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "Neodol ® 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper")
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and and outer coating coated on the first coating consisting of about 1.4 grams per 100 square inches of substrate. One of the substances of Table I, Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example IV, supra.

EXAMPLE X

Hair Spray Formulations

The following hair spray formulation is prepared by first dissolving PVP/VA E-735 copolymer manufactured by the GAF Corporation of 140 West 51st Street, New York, New York, in 91.62 grams of 95% food grade ethanol. 8.0 grams of the polymer is dissolved in the alcohol. The following ingredients are added to the PVP-VA alcoholic solution:

| | |
|---|---|
| Dioctyl sebacate | 0.05 weight percent |
| Benzyl alcohol | 0.10 weight percent |
| Dow Corning 473 fluid - Prepared by the Dow Corning Corporation | 0.10 weight percent |
| Tween 20 surfactant - Prepared by the ICI America Corporation | 0.03 weight percent |
| One of the perfumery substances as set forth in Table I of Example IV, supra | 0.10 weight percent |

The perfuming substances as set forth in Table I of Example IV add aroma characteristics as set forth in Table I of Example IV which are rather intense and esthetically pleasing to the users of the soft-feel, good-hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ® 755 N polymer (manufactured by GAF Corporation of 140 West 51st Street, New York, New York) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 wt ratio of A;B and cooled to 45° C. and 0.3 wt percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

EXAMPLE XII

Detergent Containing Encapsulated Fragrances

Perfume microcapsules are prepared using the process of U.S. Pat. No. 3,516,941 containing the perfume composition or perfume substances as set forth in Table I of Example IV and the capsules (0.3 wt %) are then mixed into an unperfumed granular laundry detergent composition containing 21% of anionic surfactant (linear $C_{12}$ alkylbenzene sulfonate), 25% of sodium tripolyphosphate, 12% of sodium silicate ($SiO_2/-Na_2O$ ratio 2.0) and 16% of sodium sulfate. The capsules are then placed in a detergent composition in accordance with the procedure of Example I at Column 11 of U.S. Pat. No. 4,145,184 the disclosure of which is incorporated by reference herein. In addition, the disclosure of U.S. Pat. No. 3,516,941 issued on June 23, 1970 is also incorporated herein by reference.

Each of the detergents has an aroma as set forth in Table I of Example IV, supra.

EXAMPLE XIII

A tobacco flavoring formulation is prepared by admixing the following ingredients:

| Ingredients | Parts by Weight |
|---|---|
| Cinnamaldehyde | 30.60 |
| Nutmeg oil EI | 0.50 |
| Dibenzyl ether | 3.70 |
| Eugenol | 1.20 |
| Coumarin | 3.00 |
| Vanillin | 1.00 |
| 3-Phenyl-4-pentenal-dimethyl acetyl | 30.00 |
| Cyclic carbonate prepared according to Example II, bulked Fractions 2 and 3 | 40.00 |

This material is added to smoking tobacco at the rate of 0.06–0.15% by weight of the tobacco.

The use of the cyclic carbonate provides to the flavor prior to smoking an excellent sweet, vanilla, coumarinic, fruity, cinnamon bark-like aroma. On smoking the smoking tobacco in standard cigarette articles using burley tobacco have sweet, fruity, virginia tobacco-like aroma and taste nuances. In addition, the flue-cured note is enhanced.

EXAMPLE XIV

Tobacco Flavor Formulation and Tobacco

A tobacco mixture is produced by admixing the following materials:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| water | 5.3 |

Cigarettes are prepared from this tobacco.
The following flavor formulation is prepared:

| Ingredient | Parts by Weight |
|---|---|
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. Half of the cigarettes are then treated with 400 or 800 ppm of the cyclic carbonate produced according to the process of Example II, bulked Fractions 2 and 3. The control cigarettes not containing the cyclic carbonate and the experimental cigarettes which do not contain the cyclic carbonate are evaluated by paired comparison and the results are as follows:

In aroma, the cigarettes containing the mixture having the cyclic carbonate are found to be prior to smoking, sweet, vanilla, coumarinic, fruity and cinnamon-like.

In smoke flavor, on smoking, the cigarettes containing the cyclic carbonate are more aromatic, and have intense sweet, fruity, Virginia tobacco-like nuances with the flue-cured note being enhanced.

In summary, the cyclic carbonate of Example II, bulked Fractions 2 and 3, enhances the flue-cured note in the tobacco on smoking and enhances the sweet, fruity, Virginia tobacco-like taste and aroma of a blended cigarette and imparts to that cigarette a Virginia-like character in smoke flavor.

EXAMPLE XV

The following mixture is prepared:

| Ingredients | Parts by Weight |
| --- | --- |
| Cyclic carbonate prepared according to Example II, bulked Fractions 2 and 3 | 8.0 |
| 3-Phenyl-4-pentenal dimethyl acetal | 3.0 |
| Cinnamic aldehyde | 8.0 |
| Orange oil | 3.0 |
| Oil of cloves | 1.0 |
| Phenyl ethyl alcohol | 5.0 |
| Ethyl alcohol | 80.0 |

The addition of the cyclic carbonate of Example II, bulked Fractions 2 and 3 to this mixture imparts to the flavor a dominating full bodied cinnamon aroma. Without the cyclic carbonate the flavor formulation is not as true cinnamon as it is with the cyclic carbonate. Furthermore, without the 3-phenyl-4-pentenal dimethyl acetal/cyclic carbonate combination, the flavor formulation is bland, lacks body and requires approximately three times as much material when added to the standard cinnamon flavor powders for use in pastry powders and cake powders. The subject flavor formulation acts as an absolute replacement for cinnamon bark, Ceylon (Cortex cinnamoni ceylanic) when used as a flavor in baking. Thus, 420 grams of the above-mentioned flavor formulation are added to the following powder cake flavor oil which is then added at the rate of 0.25% to standard cake mix and appropriately

| Mixture Gm. | |
| --- | --- |
| 27.5 | ethyl vanillin |
| 126.0 | vanillin |
| 66.0 | oil of bitter almond |
| 420.0 | oil of cinnamon bark |
| 66.0 | oil of cloves |
| 33.0 | oil of cardamon |
| 66.0 | oil of nutmeg |
| 195.5 | oil of lemon, cold pressed |
| Total 1000.0 | |

The resulting cake when baking is completed has an excellent natural cinnamon-like taste and aroma which is intense, long lasting and esthetically pleasing.

EXAMPLE XVI

The cyclic carbonate of Example II, bulked Fractions 2 and 3 is added directly to a food product prior to processing and canning. The following illustrates the beneficial flavor effect when the cyclic carbonate is added directly to several food products just prior to their comsumption:

i. Rice pudding at 10–20 ppm; creates a distinctive cinnamon flavor nuance in the rice pudding.

ii. Chewing gum originally intended to have a mint flavor; brings up cinnamon nuance at 0.5 ppm and causes the cinnamon nuance to blend favorably with the mint nuance.

iii. Baked apple; the substance is added at the rate of 4 ppm prior to baking to the sugar solution which is added to the apple. Subsequent to baking, the baked apple has an excellent cinnamon/baked apple aroma and taste which renders it esthetically pleasing and highly palatable.

iv. In applesauce at approximately 15 ppm; modifies the flavor by enhancing the apple character and creating a spice undertone while at the same time, adding cinnamon topnotes to develop the cooked apple note.

The levels of concentration of the cyclic carbonate of Example II, bulked Fractions 2 and 3 may be reduced by 40% when 3-phenyl-4-pentenal dimethyl acetal is added at the rate of from 5–100 ppm in addition to the cyclic carbonate of Example II. It should be understood further, that noticable differences in the flavor are discernable at high concentrations. At much higher levels, the flavor becomes objectionable and overly rancid tasting (e.g., 700–800 ppm).

What is claimed is:

1. A process for augmenting or enhancing the aroma or taste of a foodstuff or chewing gum comprising the step of adding to a foodstuff base or a chewing gum composition, from 0.10 parts per million up to about 50 parts per million by weight based on the total composition of a cyclic carbonate defined according to the structure:

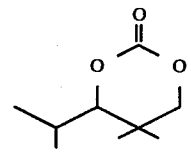

and, in addition, from 5 up to 100 ppm of 3-phenyl-4-pentenal dimethyl acetal.

2. A composition of matter comprising from 5 to 100 parts by weight of 3-phenyl-4-pentenal dimethyl acetal and from 0.1 up to about 50 parts by weight of the cyclic carbonate defined according to the structure:

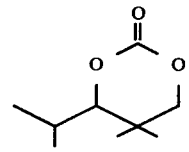

3. The composition of claim 2 wherein the weight ratio of 3-phenyl-4-pentenal dimethyl acetal:cyclic carbonate is 3:8.

* * * * *